United States Patent [19]
Peart et al.

[11] Patent Number: 5,288,954
[45] Date of Patent: Feb. 22, 1994

[54] BINAURAL STETHOSCOPE

[75] Inventors: Edward L. Peart; Gary L. Jarvis, both of Arden, N.C.

[73] Assignee: Welch Allyn, Inc., Skaneateles Falls, N.Y.

[21] Appl. No.: 6,511

[22] Filed: Jan. 21, 1993

[51] Int. Cl.⁵ .............................................. A61B 7/02
[52] U.S. Cl. .................................................... 181/131
[58] Field of Search .................... 181/131, 135, 137

[56] References Cited

U.S. PATENT DOCUMENTS

| | | | |
|---|---|---|---|
| 3,086,610 | 4/1963 | Haas | 181/131 |
| 3,108,652 | 10/1963 | Littman | 181/131 |
| 3,163,161 | 2/1965 | Littman | 181/131 |
| 3,275,099 | 9/1966 | Speelman | 181/131 |
| 3,295,631 | 1/1967 | Machlup | 181/131 |
| 3,437,172 | 4/1969 | Allen | 181/131 |
| 3,504,760 | 4/1970 | Littman | 181/131 |
| 3,746,124 | 7/1973 | Wilson et al. | 181/131 |
| 4,064,965 | 12/1977 | Brown | 181/131 |
| 4,200,169 | 4/1980 | MacDonald et al. | 181/131 |
| 4,347,911 | 9/1982 | Bertagna | 181/131 X |

Primary Examiner—Michael L. Gellner
Assistant Examiner—Khanh Dang
Attorney, Agent, or Firm—Harris Beach & Wilcox

[57] ABSTRACT

A connector for joining one end of a rigid stethoscope ear tube to a multiple leaf binaural spring within a flexible tube that is attached to the stethoscope chestpiece, having a housing for rotatably supporting one end of the rigid ear tube so that it rotates about its own axis, with the housing and springs positioned inside the flexible tube so that the ear tube and the flexible tube are placed in aural communication. The housing is biased to place a holding force on the ear tube of between 2 and 10 pounds inches torque.

12 Claims, 2 Drawing Sheets

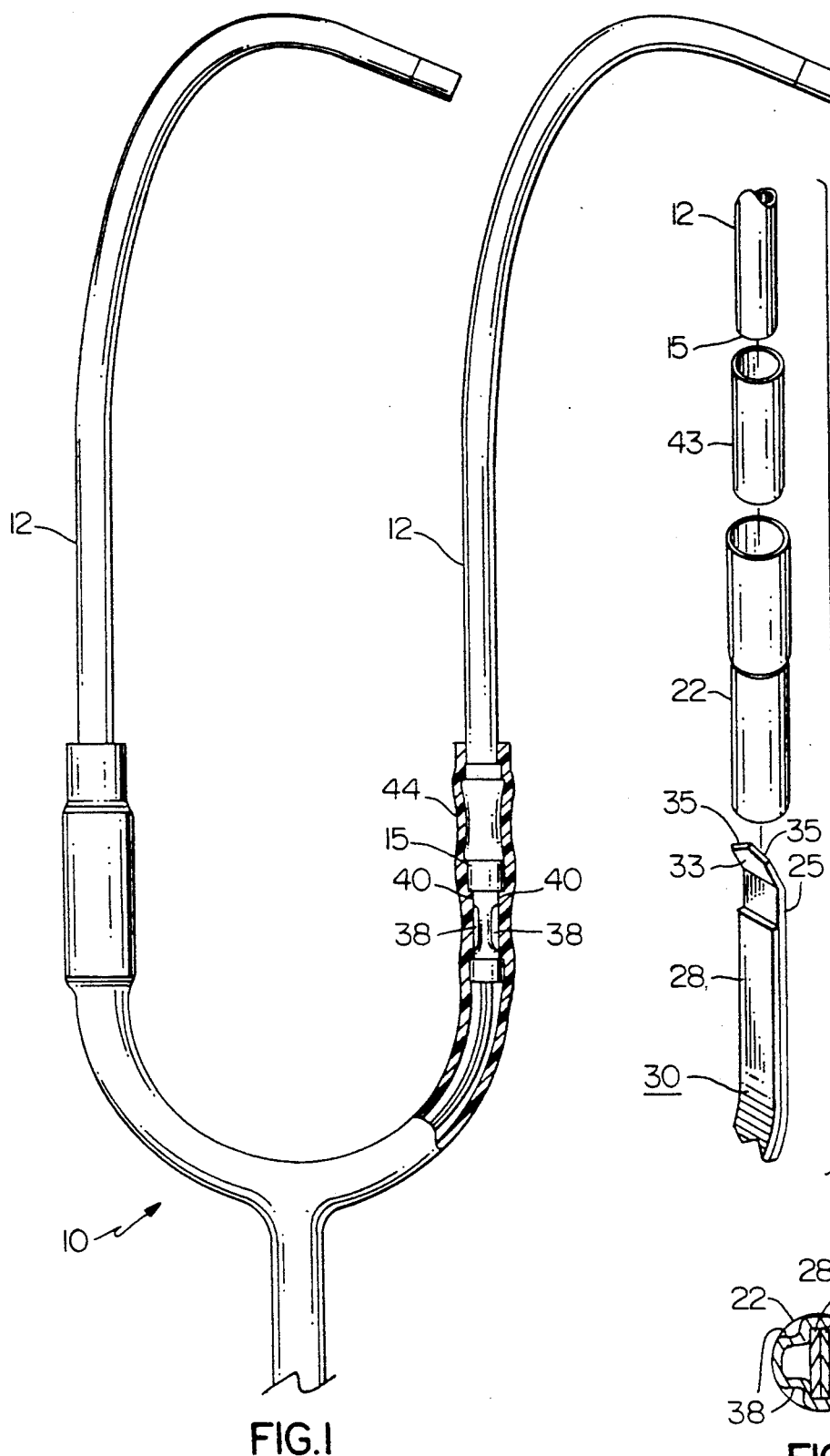

BINAURAL STETHOSCOPE

BACKGROUND OF THE INVENTION

This invention relates to a stethoscope, and more particularly to an improved binaural stethoscope.

SUMMARY OF THE INVENTION

Medical stethoscopes generally consist of a chestpiece for picking up sounds and a pair of ear tubes connected to the chestpiece, usually through separate passageways, for transmitting the sounds to each ear. The ear tubes have traditionally consisted of bent metal tubes with plastic or cushioned earplugs on the end for the comfort of the wearer and insulation of outside sound sources, together with a tensioning device for maintaining the earpieces in a configuration that provides contact with the ears of the user.

There are a number of advantages to using a dual leaf or multi-leaf spring as a tensioning device in a stethoscope. For example, in the U.S. Pat. No. 5,189,264 of one of the instant inventors (Peart) there is disclosed a multiple leaf stethoscope spring used as a tensioning device. A multiple leaf spring design allows the use of thinner springs to reduce the bending stress in the springs when they must provide a given force at a given deflection. That is, a single leaf spring of the same width can be designed to provide the same given force at the same given deflection, but the stress in the spring will be higher and the spring will reach it's yield stress at a smaller deflection than in a multiple leaf design. The multiple leaf spring has the advantage of easily engaging the ear tubes, having a longer spring life, being compact and easily bendable, and being easily and simply manufactured.

It is desirable, when using a multiple leaf stethoscope, as well as other designs, that the position of the ear tubes be rotatably adjustable. At the same time, it is not desirable that the earpiece be freely rotatable. If the earpiece can be easily moved during use, any contact with a foreign object, including the user, can cause misalignment. This results in inconvenience both to user and patient or, possibly injury. Thus, once the earpiece is rotated to a desired position with respect to the rest of the stethoscope, it should require a distinct positive effort to rotate it to a new position. Furthermore, this resistance to rotation should be inherent in the design and assembly of the stethoscope. It should not require the use of extra parts such as screws and clamps which may be lost, add to the complexity of the device, and require additional manipulations or tools to achieve the desired rotation.

Some constructions achieve at least a portion of this goal—that is general rotatability, but without the requirement of a positive effort for turning—by maintaining the earpieces in a fixed relationship to each other, but not to the spring or other tension device. It is, however, often undesirable to require that the position of both earpieces be mutually dependent. Human beings are not always entirely symmetrical in the position of their body parts. A person's left ear may be raised or lowered with respect to his or her right ear. Or one ear may be set further back on the head than the other. In addition, if there is some injury to one ear, it may be desirable to set the earpiece which would normally impinge that ear so that it does not do so. It may even be desirable to turn one earpiece so that it faces away from one user's head to accommodate the simultaneous use by a second party in, for example, teaching or training usage.

Connectors for stethoscopes which achieve rotatability without having a requirement for a positive turning effort, are directed toward a variety of tension device/ear tube combinations and each must be designed specifically to accommodate the peculiarities of the tension device/ear tube combination for which it is designed.

For example, U.S. Pat. No. 3,295,631 to Machlup discloses a curved leaf spring with outwardly extending flared ends. At least one of the flared ends contains spaced indentations in registration with corresponding indentations in each associated ear tube. The matching of indentations allows the ear tubes to be locked in preselected positions. This differs from the instant invention which must accommodate two leaf springs rather than one. The use of multiple leaf springs necessitates additional considerations in design, since the springs must maintain a constant relation to one another while allowing rotation with respect to the ear tube. In addition, the instant inventions allows positioning of the ear tubes at any position, rather than just at predefined positions.

U.S. Pat. No. 3,275,099 to Speelman shows an ear tube with annular grooves and a corresponding tubular leaf spring end which has a tapers so as to clamp in the ear tube groove. This construction would not be possible with a multiple leaf stethoscope.

U.S. Pat. No. 3,163,161 to Littmann describes the connection of earpieces to a dual leaf spring stethoscope. This connection allows the ear tubes to be secured in selected angular position with respect to one another. This involves the angle with respect to the plane of the stethoscope however—that is how far apart the ends of the ear tubes are positioned. It does not allow for rotation of the ear tube ends about their own axes and out of the plane of the stethoscope.

None of the art described above provides for a multiple leaf spring stethoscope where the ear tubes are independently rotatable to any position and yet tend to remain in a fixed position when not forcefully rotated.

It is therefore a primary object of the present invention to provide a binaural stethoscope with a multiple leaf spring whose ear tubes may be positioned independently of one another.

It is a further object of the present invention to provide a binaural stethoscope with a multiple leaf spring whose ear tubes may be positioned independently of one another and, once positioned, will remain fixed in position until forcefully moved.

These and other objects of the present invention are attained by a stethoscope having a connector for joining one end of a rigid ear tube to a multiple leaf binaural spring within flexible tube that is attached to the stethoscope chestpiece, the connector including a housing for rotatably supporting one end of the rigid ear tube so that said ear tube rotates about its axis, the housing and springs positioned inside the flexible tube so that the ear tube and the flexible tube are placed in aural communication, and biasing the housing to place a holding force of between 2 and 10 pound-inches torque on the ear tube.

BRIEF DESCRIPTION OF THE DRAWINGS

For a better understanding of these and other objects of the present invention, reference is made to the detailed description of the invention which is to be read in conjunction with the following drawings, wherein:

FIG. 1 is a cross section elevation of the preferred embodiment of the stethoscope of this invention showing a portion of the stem of the "Y" shaped sound tube broken away and without the stethoscope head.

FIG. 2 is an enlarged fragmentary exploded view of the end of the binaural spring member of the stethoscope of FIG. 1, the end of the rigid ear tube member, the sheath, and torque sleeve joining the two.

FIG. 5 is a cross section of the stethoscope sleeve taken along line 1—1 of FIG. 4.

DETAILED DESCRIPTION OF THE INVENTION

Figure 3:
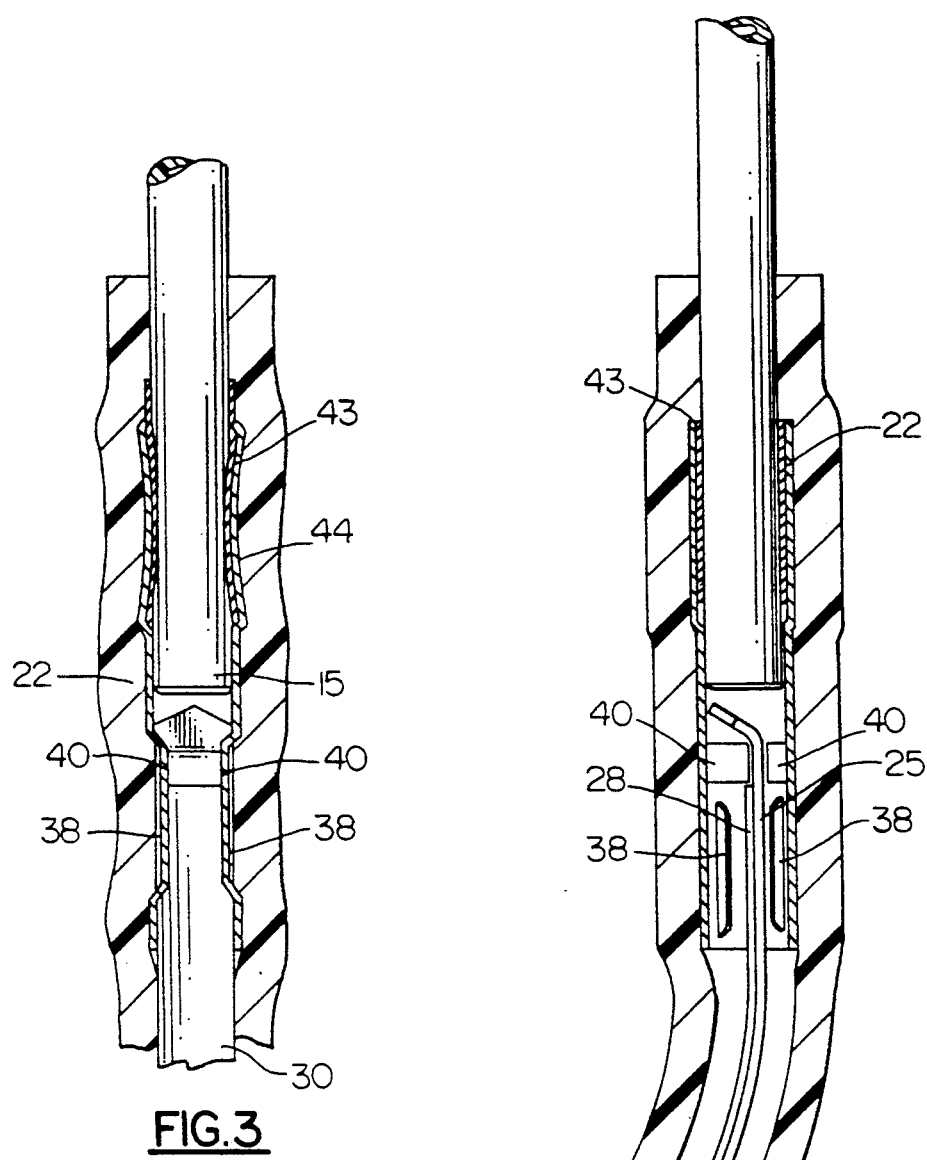
FIG. 3 is an enlarged perspective detail of the end of the binaural spring member and end of the rigid tube member with the sheath and sound tube stem broken away of the stethoscope of FIG. 1.

Referring now to FIG. 1, a preferred embodiment of this invention is shown, as applied to a dual leaf spring stethoscope. It can be seen that the two ear tube members 12—12 of the stethoscope 10 can be rotated at any angle to the body of the stethoscope and to each other. As can be better seen in FIG. 2, in the preferred embodiment of the stethoscope of this invention, the primary spring 25 and secondary spring 28 of the dual leaf spring assembly 30 fit within a tubular connecting sleeve 22 which also accommodates the tip 15 of the ear tube member 12. Between the tubular connecting sleeve 22 and the ear tube member 12 is a polyurethane sleeve 43, discussed in more detail below. The tubular connecting sleeve can accommodate more than two leaf springs as in, for example, a triple leaf spring design.

Figure 4:
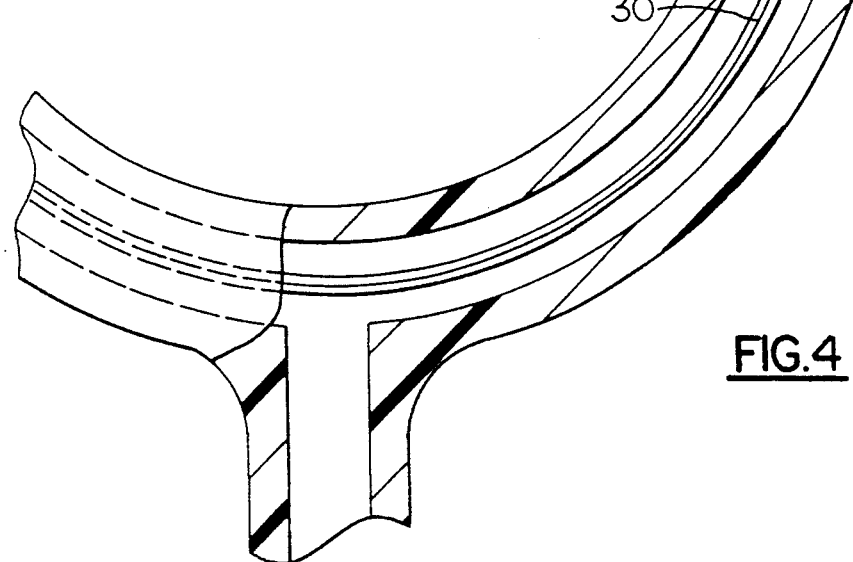
FIG. 4 is an enlarged front view of the stethoscope of FIG. 1, showing half of the binaural spring member and end of the rigid tube member with the sheath and sound tube stem broken away.

Referring, now, to FIG. 4, it can be seen that the inner or secondary spring 28 nests against the outer primary spring 25, the secondary spring 28 being positioned closer to the inside wall of the "U" shaped spring assembly 30 and the primary spring being positioned closer to the outside wall of the "U" shaped spring assembly 30. The primary spring 25 is somewhat longer than the secondary spring 28. A length difference of between 0.5 and 1.5 inches is preferable. If more than two springs are used their relative lengths can be adjusted appropriately to retain the same relationship of longer primary spring. This unequal length allows the end 33 of the primary spring to be bent inward at approximately a 120° angle to itself. The primary spring end 33 is also clipped at the corners 35 at an angle of approximately 45° so that it may be inserted into the tubular connecting sleeve 22.

Referring now, to FIG. 4 the dual leaf spring assembly 30 is held in its proper nested position by sliding the tubular connecting sleeve 22 over the upper end of the spring pair and placing a permanent crimp 38 in the sleeve at a position where it contains the ends of the springs. The wall of the sleeve is forced inward and around the edges of the springs to effectively grip the springs and thus prevent rotation of the springs inside the sleeves, as can be better seen in FIG. 5. Since the primary spring 25 is longer than the secondary spring 28 it is necessary to have one set of punches 40—40 positioned along the length of the primary spring where it extends beyond the secondary spring to force the sleeve wall to tightly grip the primary spring by itself and adjacent to the bent end of the spring. This deformed section of the sleeve effectively prevents the primary spring from being pulled axially out of the sleeve. When the tubular connecting sleeves have been permanently crimped on both ends of the binaural spring pair 30, the secondary spring 25 is effectively trapped within the assembly. It is necessary that the secondary spring 28 be allowed to move a short distance along the length of the primary spring 25, but that freedom of motion must not be sufficient for it to be disengaged from the tubular connecting sleeves 22. This freedom to move within limits enables the two springs to evenly share the load imposed upon them when in use. The same principle can be applied to stethoscopes with more than two leaf springs.

Thus the primary and secondary springs making up the spring assembly 30 are held by the tubular connecting sleeve 22 in such a way that the springs cannot rotate within the sleeve nor can they be withdrawn from the sleeve through the application of a reasonable amount of force.

FIG. 1 shows that the crimping of section 44 of the tubular connecting sleeve onto the end of the ear tube is created in such a way so as to produce an hourglass shape in both the tubular connecting sleeve and the ear tube. Since the inside diameter of the deformed tubular connecting sleeve at the narrow segment of the hourglass shape is less than the undeformed outside diameter of the ear tube tip 15, the ear tube 12 cannot be withdrawn from the tubular connecting sleeve 22. Further, in the preferred embodiment, the tubular connecting sleeve 22 is fabricated of stainless steel which has a lower strain for a given level of stress than the aluminum ear tube 12. Thus there is a residual force between these two components after the deforming assembly operation. This force generates a friction force between the two components which resists the rotation of the ear tube within the tubular connecting sleeve 22.

To control the level of this friction force so that the force needed to turn an eartube is between 2 and 10 pound inches torque, a thin polyurethane sleeve 43 is placed between the ear tube 12 and the tubular connecting sleeve 22. This polyurethane sleeve serves to prevent direct metal to metal contact in the deformed area. The polyurethane sleeve 43 thus reduces the coefficient of friction and subsequently the force required to rotate the ear tube 12 into a range suitable for use.

Testing of assemblies described has shown that to increase the life of the tubular connecting sleeve joint it is desirable to control the interface where the relative motion takes place. If the polyurethane sleeve 43 moves relative to the steel tubular connecting sleeve 22 the polyurethane sleeve 43 has a strong tendency to migrate axially out of the tubular connecting sleeve 22 toward the ear tube 12. When this axial motion takes place the force required to rotate the ear tube 12 varies widely and ultimately drops to zero when the polyurethane sleeve has moved completely out of the tubular connecting sleeve 12.

Two features of this design prevent this result. The open end of the tubular connecting sleeve 22 is deformed inward at approximately 45° toward the ear tube and to within a few thousandth of an inch of the ear tube to trap the polyurethane sleeve and impede its axial movement. In addition, a phosphorylated mono and diglyceride solution is applied on the outside of the aluminum ear tube 12 to selectively lower the coefficient of friction at this interface with the polyurethane sleeve 43. This helps assure that when the ear tube 12 is rotated within the tubular connecting sleeve 22, the polyurethane sleeve 43 will not itself rotate within the tubular connecting sleeve 22 and thus will not migrate axially to free itself from its position in the tubular connecting sleeve 22.

Another advantage of the polyurethane sleeve 43 is that it causes the connection to have a relatively high breakaway force—that is it is harder to start turning the ear tube 12 with respect to the tubular connecting sleeve 22, than it is to continue such motion once it has begun. Thus it is unlikely that the tube will be turned accidentally.

While this invention has been explained with reference to the structure disclosed herein, it is not confined to the details set forth and this application is intended to cover any modifications and changes as may come within the scope of the following claims:

What is claimed is:

1. A compact connector for joining one end of a rigid stethoscope ear tube to a multiple leaf binaural spring within a flexible y-tube that connects said rigid ear tube to the stethoscope chestpiece, the connector including:
    a housing for rotatably supporting one end of said rigid ear tube so that said ear tube rotates about the axis of said ear tube, said housing having an upper edge, and said housing being connected to the multiple leaf binaural spring so that said ear tube and said flexible y-tube, together with the multiple leaf binaural spring are placed in aural communication; and
    biasing means associated with said housing for placing a holding force on said ear tube, to resist a rotating motion of said ear tube within said housing, said force being between 2 and 10 pound inches torque.

2. The connector of claim 1 wherein said multiple leaf binaural spring is a dual leaf binaural spring.

3. The connector of claim 1 wherein a rotatably supported ear tube is set inside said housing so that said rotatably supported ear tube is biased within the housing but may not be withdrawn from said housing by crimping said housing onto said rotatably supported ear tube so as to produce a corresponding hourglass shape in both said housing and said rotatably supported ear tube.

4. The connector of claim 3 wherein said biasing means is comprised of a thin plastic sleeve inserted between the rotatably supported ear tube and the housing to prevent direct member to housing contact so as to control the level of friction between said rotatably supported ear tube and said housing.

5. The connector of claim 4 wherein the upper edge of the housing is deformed inwardly at approximately 45° toward said rotatably supported ear tube and to within a few thousandth of an inch of said rotatably supported ear tube to trap the plastic sleeve in order to impede the axial motion of the plastic sleeve.

6. The connector of claim 4 wherein the outside of said rotatably supported member is coated with a lubricant in order to selectively lower the coefficient of friction at an interface between said ear tube member and said plastic sleeve to inhibit the axial motion of the plastic sleeve.

7. The connector of claim 4 wherein said plastic sleeve is composed of polyurethane.

8. The connector of claim 6 wherein said lubricant is a solution of phosphorylated mono and diglyceride.

9. The connector of claim 2 wherein said binaural spring is comprised of two leaf springs of generally "U" shape wherein said springs are held permanently in place in said housing by permanently crimping said housing around the edges of said springs.

10. The connector of claim 2 wherein the load imposed when said stethoscope is in use is evenly shared by said leaf springs.

11. The connector of claim 10 wherein the load imposed when said stethoscope is in use is evenly shared by said leaf springs and said even sharing of load among said leaf springs is accomplished by:
    an outer primary spring fabricated to be from 0.5–1.5 inches longer than an inner secondary spring, with the ends of said outer spring bent inward and having the corners of said ends clipped at an angle to allow insertion into said housing;
    said outer spring being bent inward at an angle of approximately 120° and clipped off said corners at an angle of approximately 45°;
    said housing being deformed to crimp around the edges of said primary spring where said primary spring extends beyond said secondary spring, thus preventing the primary spring from being pulled axially out of the housing;
    the bottom end of said housing being permanently crimped thus allowing a short range of movement of said secondary spring while retaining said secondary spring within said housing.

12. The connector of claim 1 wherein said ear tube is set inside said housing so that said ear tube may be controllably rotated within the housing but may not be withdrawn from said housing by crimping said housing onto said ear tube so as to produce a corresponding hourglass shape in both said housing and said ear tube.

* * * * *